United States Patent [19]

Lewkowicz

[11] Patent Number: 4,594,731
[45] Date of Patent: Jun. 10, 1986

[54] ELECTRONIC STETHOSCOPE

[75] Inventor: Shlomo Lewkowicz, Salt Lake City, Utah

[73] Assignee: University of Utah, Salt Lake City, Utah

[21] Appl. No.: 670,475

[22] Filed: Nov. 9, 1984

[51] Int. Cl.⁴ .............................................. A61B 7/04
[52] U.S. Cl. ..................................... 381/67; 128/715
[58] Field of Search ................... 381/67, 98; 128/715; 179/107 FD

[56] References Cited

U.S. PATENT DOCUMENTS

| | | | |
|---|---|---|---|
| 3,651,798 | 3/1972 | Egli | 381/67 |
| 3,732,868 | 5/1973 | Willems | 381/67 |
| 4,220,160 | 9/1980 | Kimball | 381/67 |
| 4,446,872 | 5/1984 | Marsoner | 128/715 |

FOREIGN PATENT DOCUMENTS 158695  12/1978  Netherlands ........................ 128/715

*Primary Examiner*—Gene Z. Rubinson
*Assistant Examiner*—L. C. Schroeder
*Attorney, Agent, or Firm*—Spensley Horn Jubas & Lubitz

[57] ABSTRACT

An electronic transducer in which the detected sounds are frequency multiplied to place them in a more favorable position for hearing within the auditory range, and in which lateral modulation by means of electrocardiogram signals is achieved to give a perception of physical space to the detected sounds.

16 Claims, 10 Drawing Figures

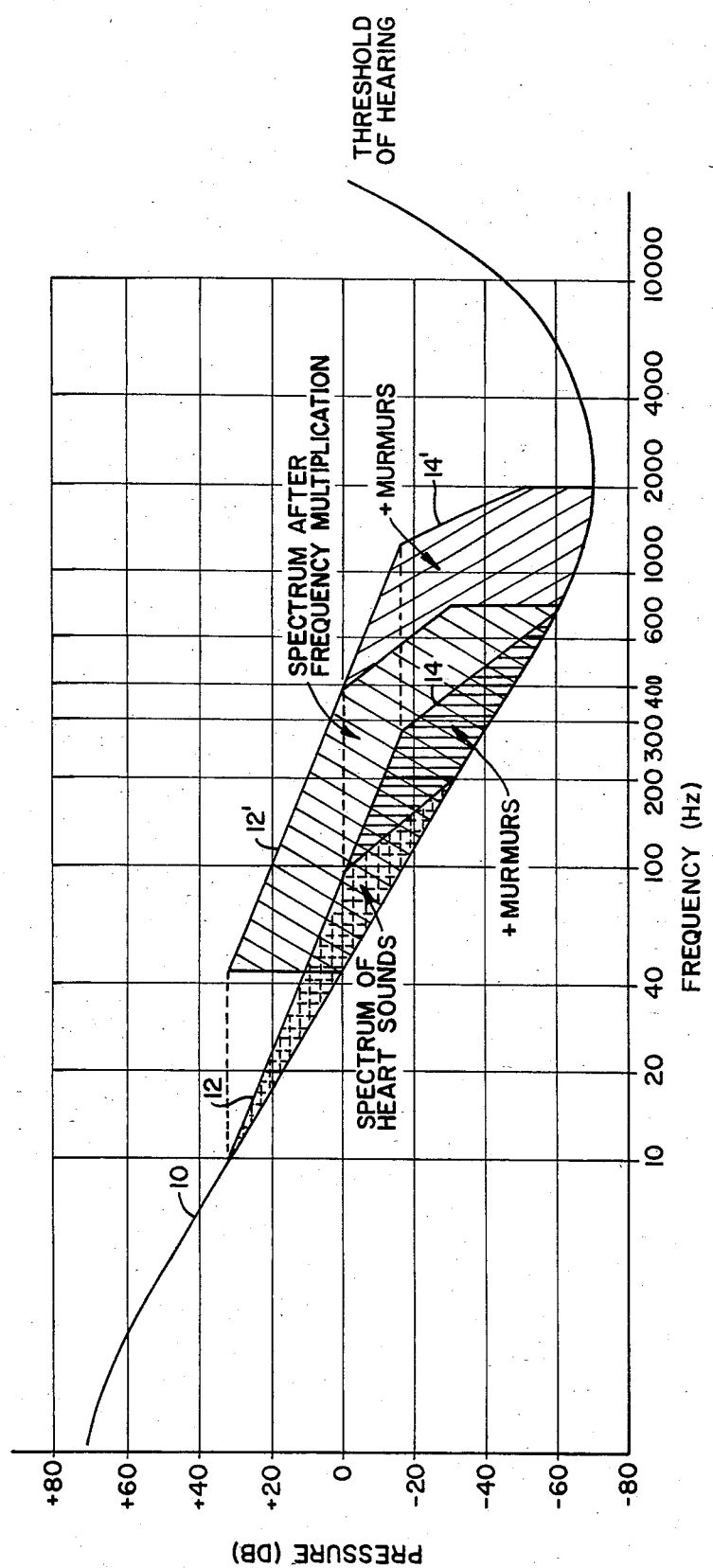
FIG._1.

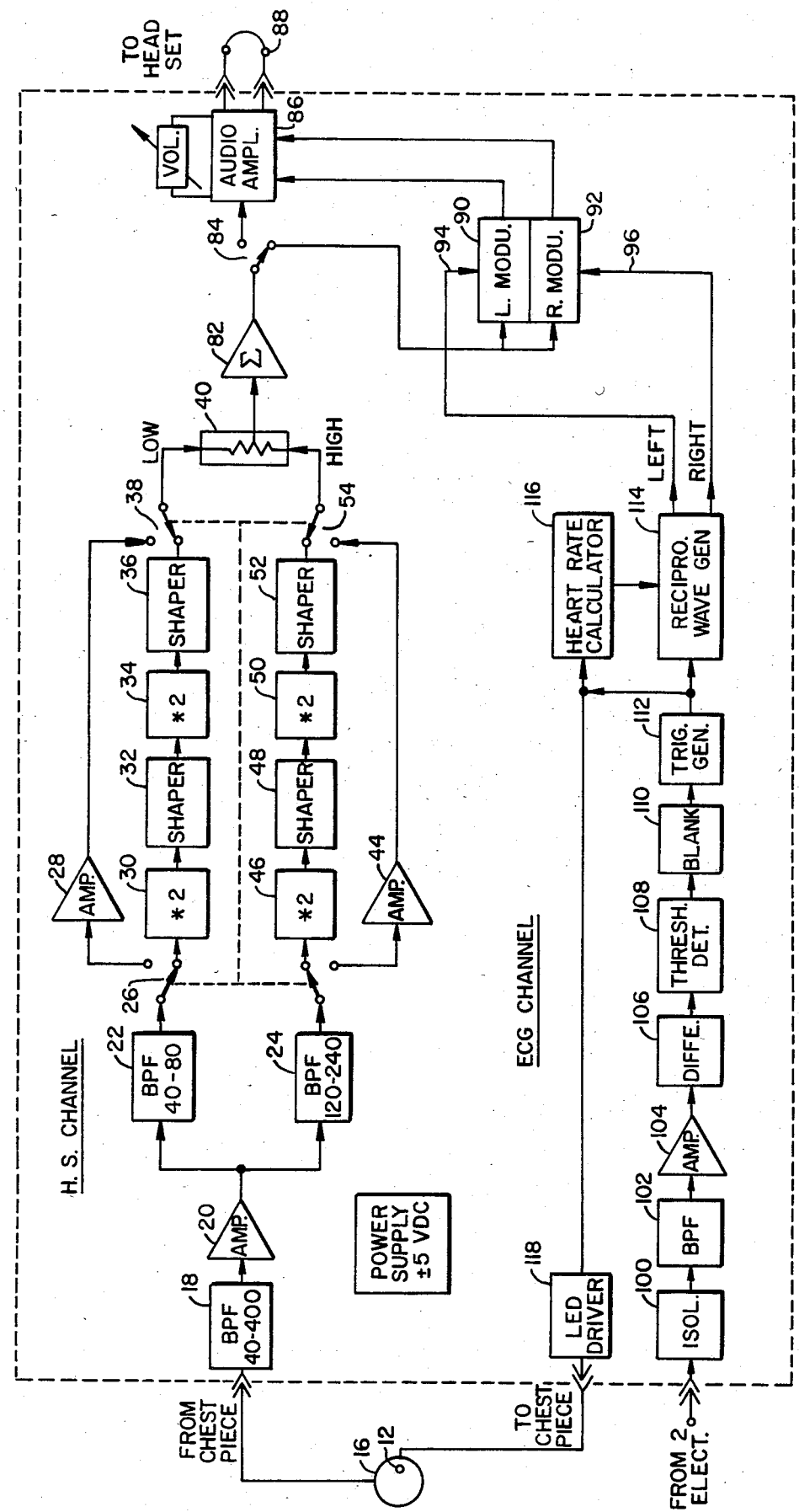
FIG._2.

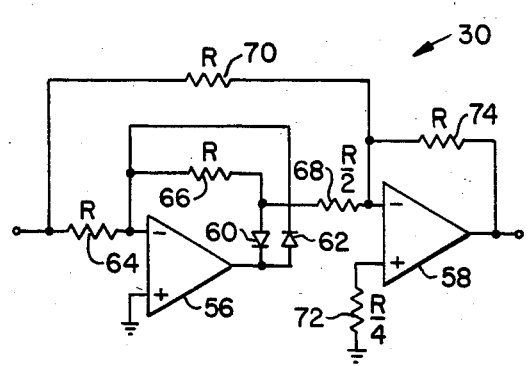
FIG._3.
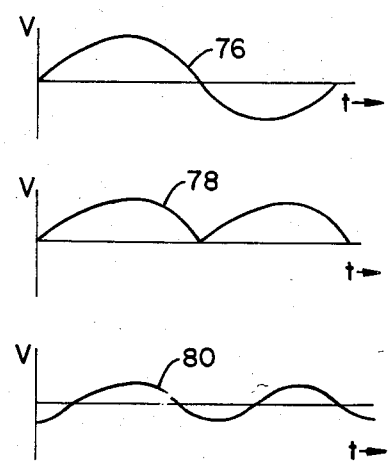
FIG._4.
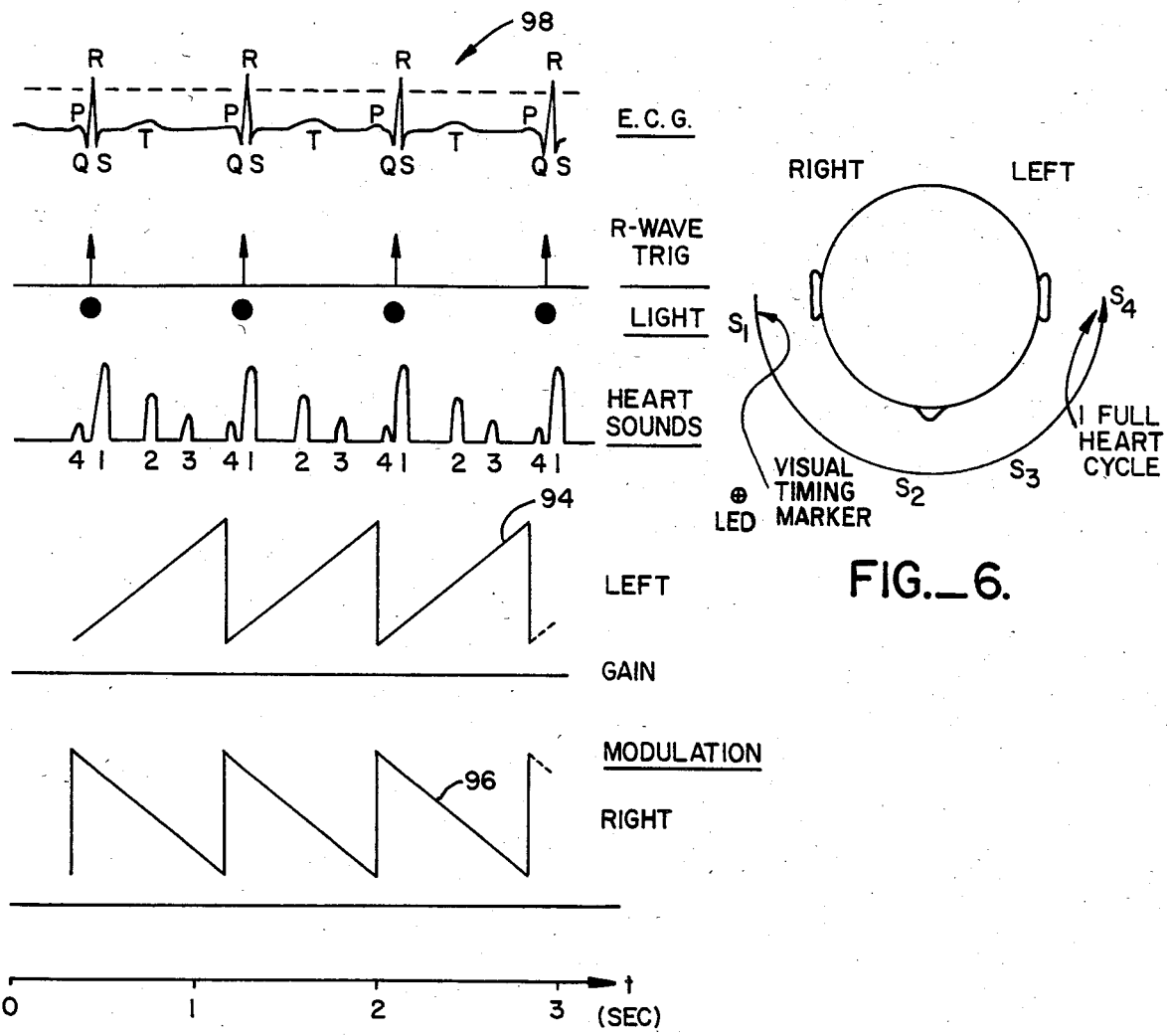
FIG._5.
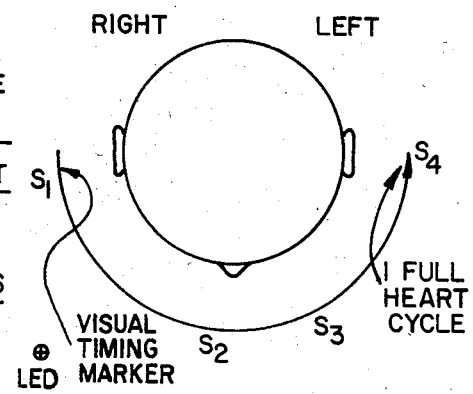
FIG._6.

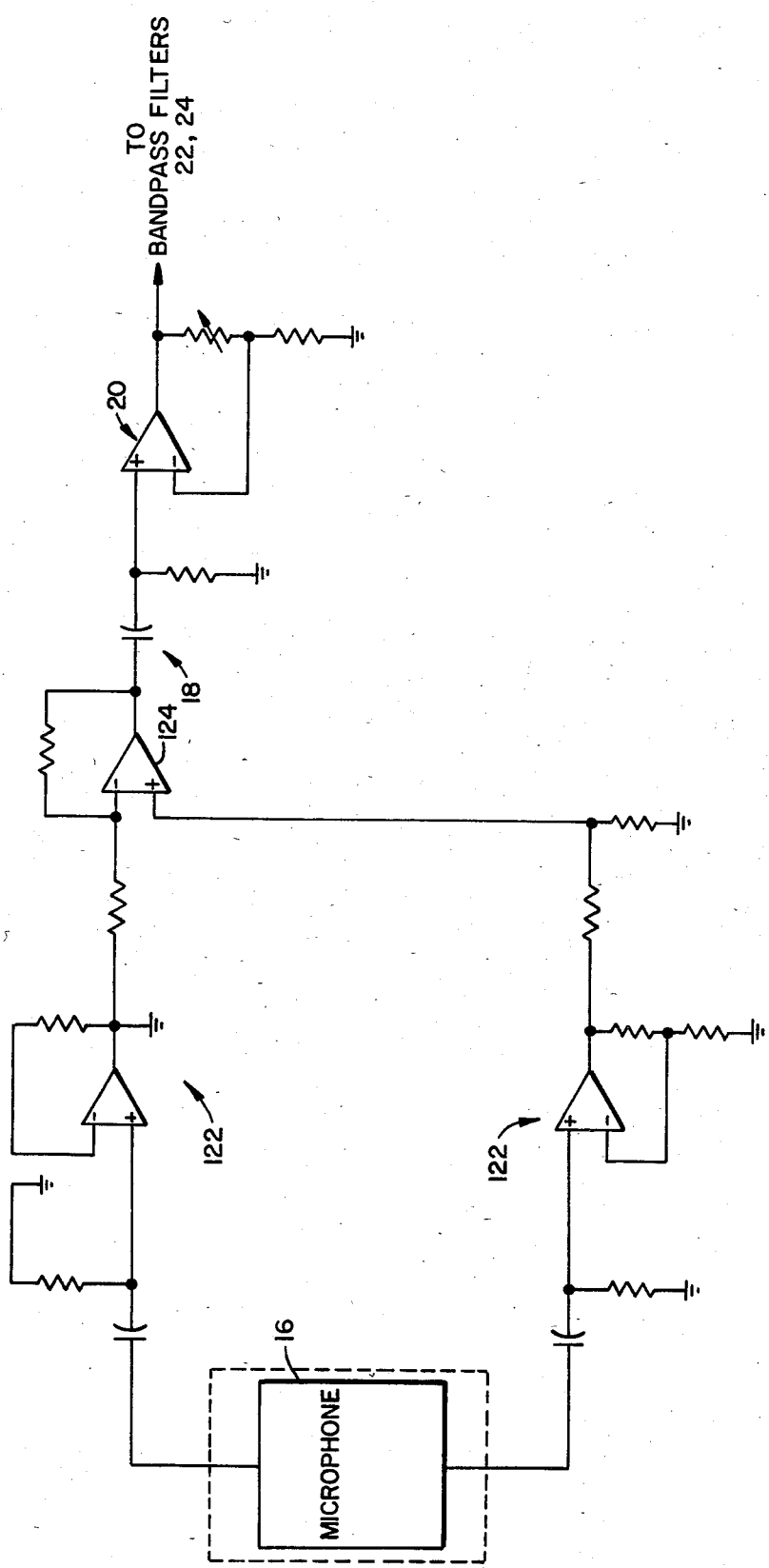
FIG._7.

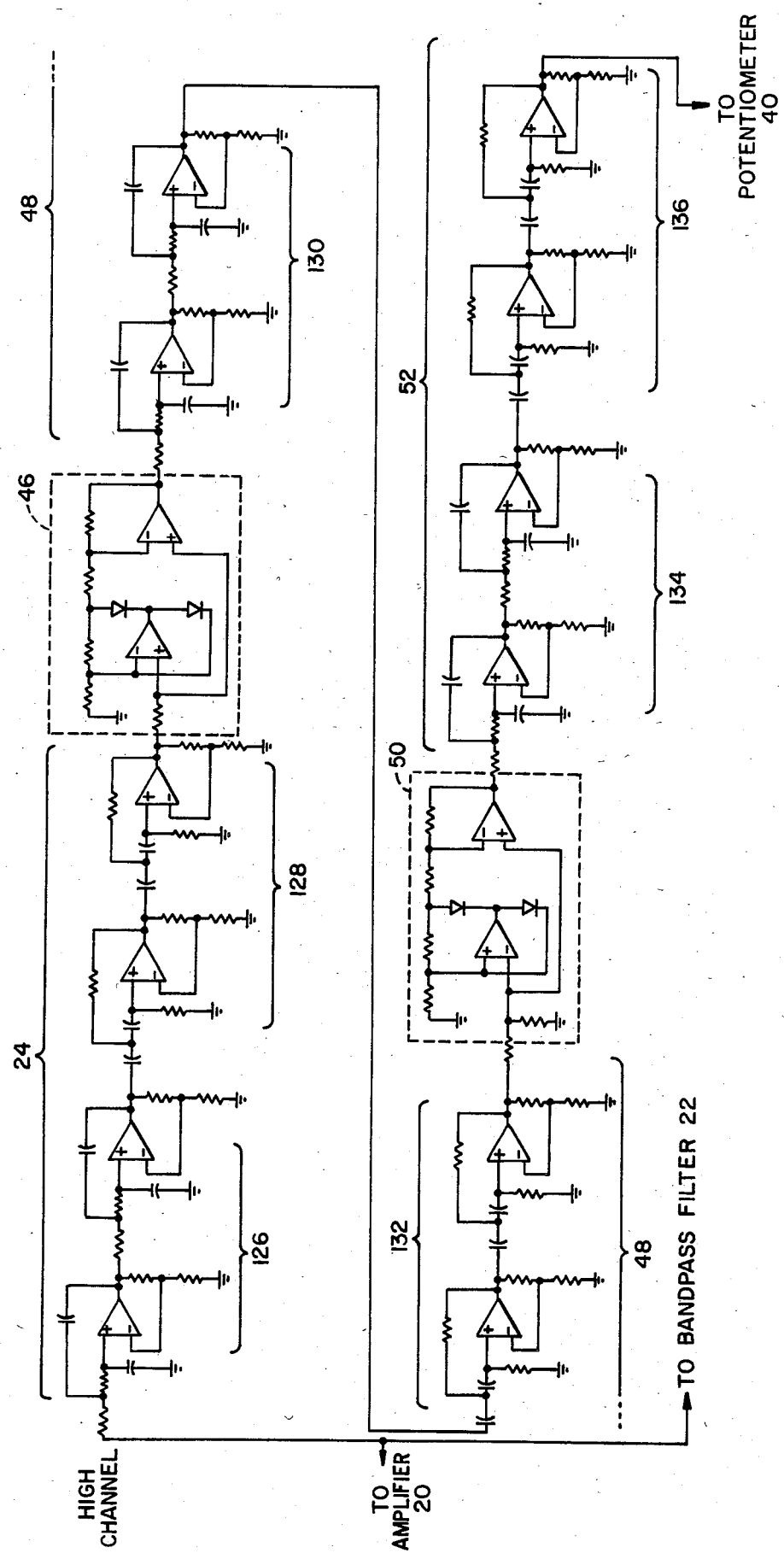
FIG._8.

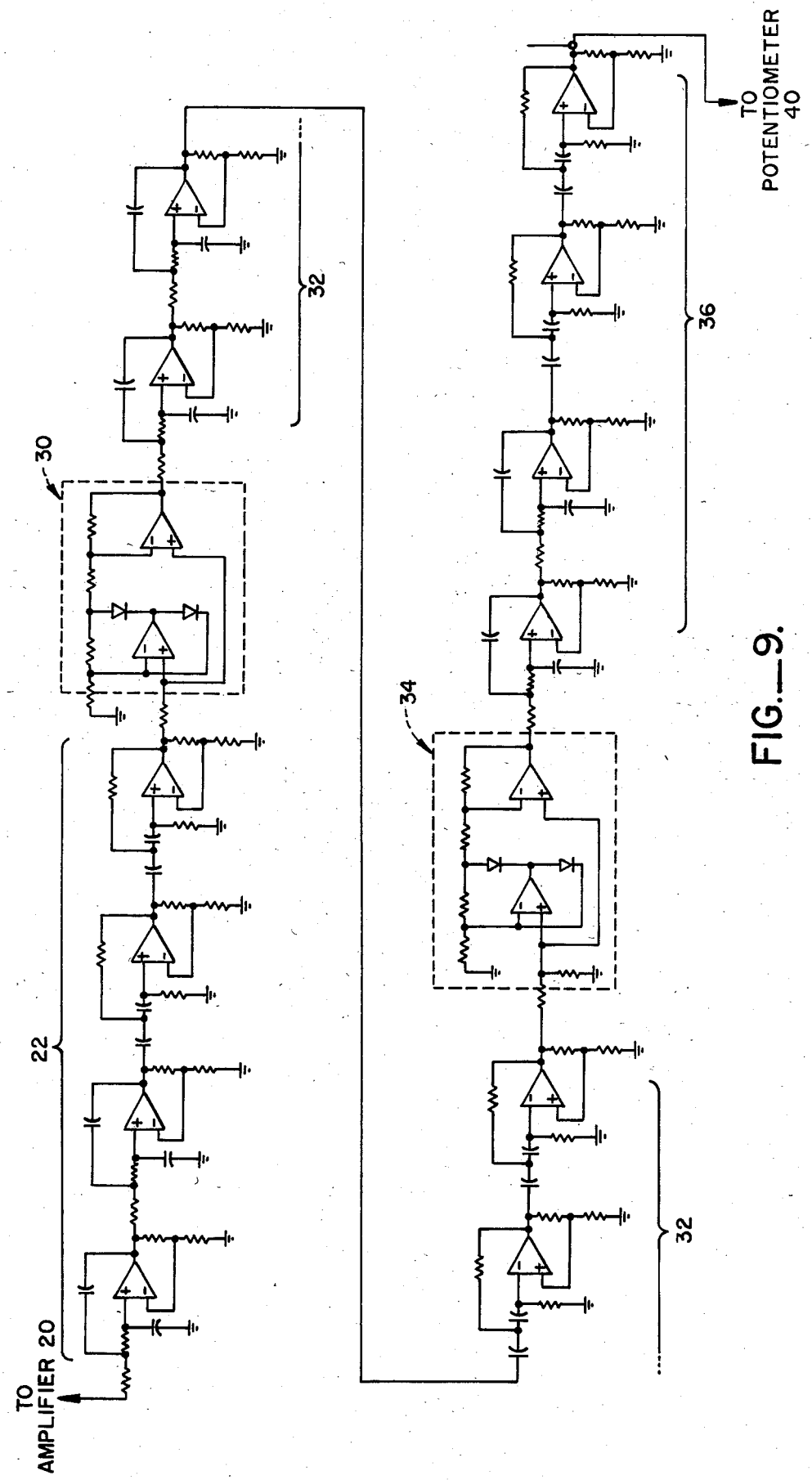
FIG._9.

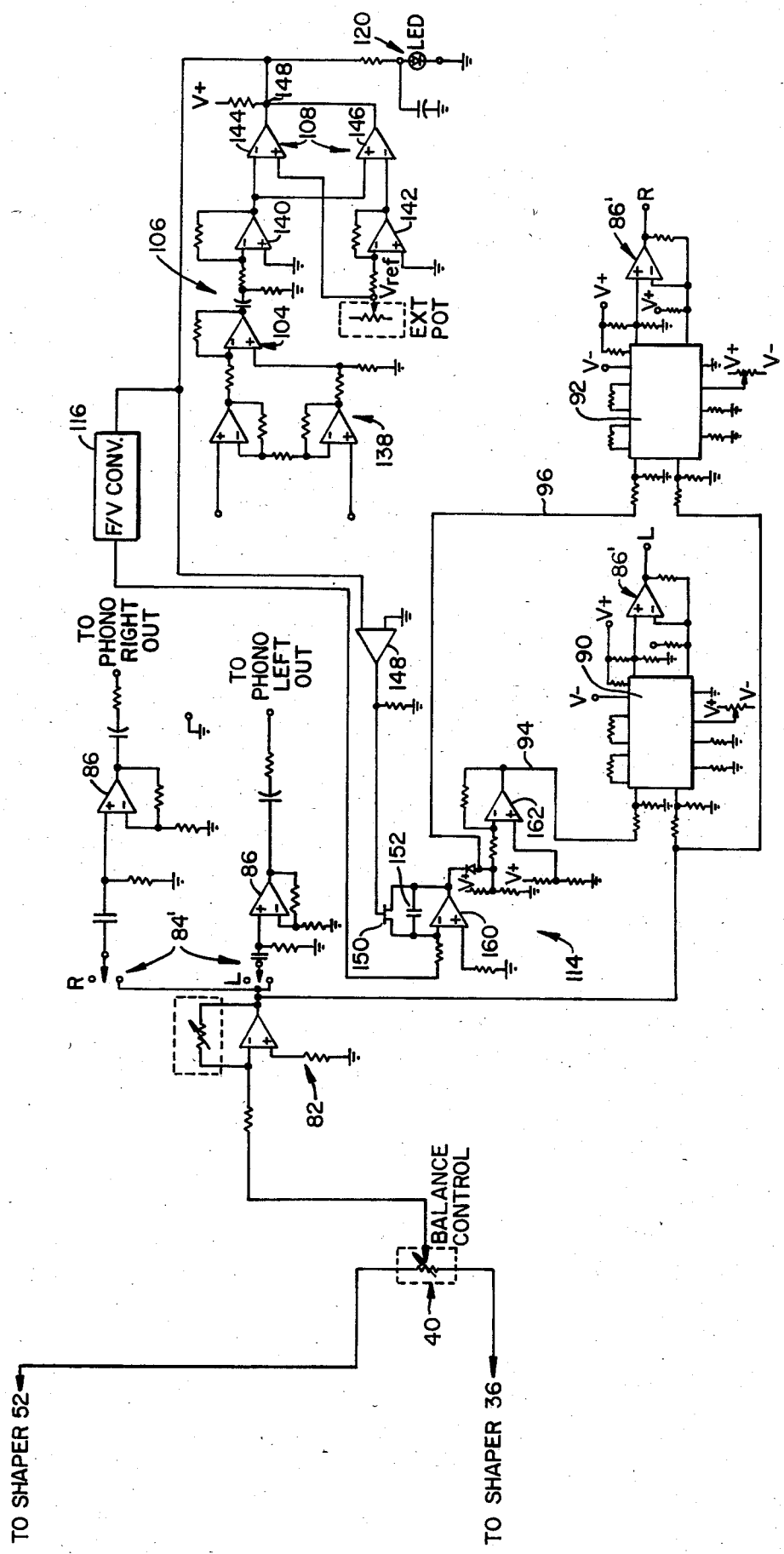
FIG._10.

4,594,731

ELECTRONIC STETHOSCOPE

DESCRIPTION

1. Technical Field

This invention relates to a stethoscope and, more particularly, to an electronic, cardiac stethoscope.

2. Background Art

It has long been recognized that many of the sounds detected by a stethoscope fall outside of the auditory range and thus cannot be heard without electronic processing. This is particularly true in detection of cardiac sounds. There have been a number of devices which have attempted to overcome this problem either by simply amplifying the sounds or by electronically shifting the sounds to a higher frequency. In some of these devices, ambient sounds are also picked up and amplified, making discrimination difficult.

The threshold of hearing for a normal human listener rises dramatically below 2000 Hertz. Unless the frequency of the detected signal is boosted considerably, to be near this point, much of the signal will remain undetected by the listener. The difficulty with the frequency shifting scheme is that heretofore the shifting has been done arithmetically so that, in effect, each frequency component of the detected signal simply has the same addition to its frequency. That is, for example, sound components at 20, 50 and 60 Hertz may be reproduced at 1020, 1050 and 1060 Hertz if they are shifted by 1000 Hertz. One difficulty with this is that such frequency shifted sounds at the higher frequencies will seem crowded together and thus less detectable individually by the listener.

Still another problem in cardiac stethoscopes is that it is often difficult to relate the particular sounds being heard to the mechanical events within the heart cycle. Thus, for example, it is difficult for the listener to determine whether a heart murmur is occurring at the end of the heart cycle or at the very beginning of the heart cycle. Various attempts have been made to overcome this problem, such as by simultaneously plotting an electrocardiogram and a phonocardiogram, that is the heart's electrical signals and its sound signals are plotted beside each other as the heart beats, in order to aid the doctor in making a correct diagnosis. Unfortunately, such strategems also make it difficult for the listener to precisely position the stethoscope on the patient's body and look at the read-outs of the instruments at the same time.

DISCLOSURE OF INVENTION

The above and other problems of detecting low frequency sounds by means of a stethoscope are overcome by the present invention of an electronic stethoscope which comprises a phono-transducer for converting physical vibrations into corresponding alternating current electrical signals, frequency multiplier means for multiplying the frequency of said signals by a predetermined number, and reproducer means supplied with said frequency multiplied signals for audibly reproducing said frequency multiplied signals. In the preferred embodiment, the phono-transducer signals are multiplied by a predetermined integer. This shifts the entire detected spectrum of sounds upward while expanding the bandwidth of the detected sounds so that they more easily are perceived by the listener.

In the preferred embodiment of the invention, an electrocardio detection means is also employed for detecting and amplifying electrical signals generated. A detector is supplied with the amplified heart electrical signals for detecting the QRS wave thereof and for producing a trigger control pulse in response thereto. Stereophonic amplification circuitry is supplied with the frequency multiplied signals detected by the phono-transducer and drives stereophonic sound reproducers.

The stereophonic amplification circuitry has left and right amplification channels whose outputs are independently modulatable by left and right control signals, respectively. A reciprocal wave generator is supplied with the trigger control pulse for generating, in response thereto, the left and right control signals for the stereophonic amplification means. These control signals have waveforms which are inverted with respect to each other. The result is that the amplified, frequency multiplied phono-transducer signals shift from one reproduction channel to the other over the period of each heart beat to give a perceived effect to the listener of having the heart sounds seem to come from various locations in front of the listener, sweeping from right to left for example. It is as though the entire heart beat were being stretched out in physical space and beginning at, for example, the listener's right and travelling over a physical distance to the listener's left. This makes it much easier for the doctor to detect when, during the heart cycle, a particular sound is occurring.

In order to further aid in this detection, a visual indicator is triggered by the QRS trigger control pulse produced by the electrocardio detection means. Preferably the indicator is placed on the phono-transducer.

Because the heart rate can change during this detection operation, a heart rate calculator circuit, which is supplied with the trigger control pulse, is further included for determining the heart rate and for adjusting the rate of change, with respect to time, of the left and right gain control signals as a predetermined function of the detected heart rate. Thus, the reciprocal wave generator generates ramp waveforms for the left and right control signals which waveforms have oppositely directed slopes. If the heart rate increases, the heart rate calculator increases the absolute value of the slope of the left and right control signals and if the heart rate decreases, the heart rate calculator decreases the absolute value of the slope of the left and right control signals, so that for any particular heart beat frequency a full right to left stereophonic effect is achieved.

In a preferred embodiment of the invention, the frequency multiplier circuit further comprises a plurality of bandpass filters for dividing the phonotransducer signals into a plurality of ranges of frequency components which are separately frequency multiplied. A balance potentiometer allows the listener to select whether the higher or the lower frequency range is primarily amplified or whether both ranges are amplified equally.

It is therefore an object of the present invention to provide an electronic stethoscope which frequency multiplies detected sounds into the audible range.

It is yet another object of the invention to provide an electronic stethoscope in which detected heart sounds are heard stereophonically and are amplified in such manner that the listener perceives them as having a spatial separation during the heart cycle.

It is yet a further object of the invention to provide an electronic stethoscope in which a visual indicator is mounted on the chest piece of the stethoscope to give the user a visual indication of the beginning of the heart beat.

The foregoing and other objectives, features and advantages of the invention will be more readily understood upon consideration of the following detailed description of certain preferred embodiments of the invention, taken in conjunction with the accompanying drawings.

BRIEF DESCRIPTION OF THE DRAWINGS

FIG. 1 is a diagram showing sound pressure in decibels as the ordinate, and logarithmic frequency as the abscissa, with the threshold of human hearing being plotted along with the spectrum of natural heart beat and murmur sounds;

FIG. 2 is a block diagram of the electronic stethoscope according to the invention;

FIG. 3 is a schematic diagram of the frequency doubling circuit portion of the block diagram shown in FIG. 2;

FIG. 4 depicts waveform diagrams showing the result of frequency doubling;

FIG. 5 is a series of waveform diagrams for use in explaining the operation of the invention;

FIG. 6 is an illustration for use in explaining the operation of lateral, audio modulation according to the invention; and FIGS. 7 to 10, inclusive, together constitute a schematic diagram of an electronic stethoscope according to one embodiment of the invention.

BEST MODE FOR CARRYING OUT THE INVENTION

Referring now more particularly to FIG. 1, the dependence of hearing sensitivity on frequency is illustrated. The curve 10 depicts the threshold of human hearing, that is the auditory range. It can be seen that relatively low frequency sounds are not detected unless they are quite loud, on the order of 30 dB (at standard pressure levels, "SPL"). In contrast to this, sounds having minus 60 dB and below are audible if they are at a frequency of approximately 2000 Hertz.

The spectrum of heart sounds which rises above the threshold of hearing, i.e. the audible heart sounds, is illustrated by waveform 12. The waveform 14 shows the area of audible heart murmur sounds.

The advantages of frequency multiplication over such earlier techniques as frequency shifting (described in U.S. Pat. No. 4,220,160—Kimball et al.) are that a new heart sound is produced with a higher and wider frequency bandwidth. This allows for easier detectability of heart sound components due to their higher pitch, and an enhanced resolution of different frequency components due to the effective spreading out of the heart sounds to a wider band frequency.

Again with reference to FIG. 1, assume that the heart sound spectrum, including murmurs, has a frequency range from 40 to 500 Hertz. If these heart sounds are multiplied by a factor of 4, the new frequency range will be between 160 to 2000 Hertz. This is illustrated by the waveforms 12' and 14', which correspond to the frequency multiplied waveforms 12 and 14, showing the spectrum of heart sounds and murmurs. All of the relative intensity information is maintained within the heart sound because the frequency multiplication does not affect the shape of the original heart sound envelope, when plotted logarithmically. Moreover, because the sound spectrum has been shifted over the dip of the threshold of hearing waveform, more of the heart sounds are heard than at the original, lower frequencies Referring now more particularly to FIG. 2, heart sounds are detected and are converted into electrical signals by a contact phono-transducer 16 and are supplied through a 40 to 400 Hertz bandpass filter 18 to the input of an operational amplifier 20. Use of a contact transducer greatly reduces pick-up of ambient sounds. The output of the amplifier 20 is divided and is sent to two separate bandpass filters 22 and 24 which have frequency ranges, respectively, of 40 to 80 Hertz and 120 to 240 Hertz. The output of the bandpass filter 22 is supplied to the pole terminal of a single pole doublethrow switch 26 which, depending on the position of the switch, supplies the output of the bandpass filter 22 to the input of an amplifier 28 or to the input of a frequency multiplier circuit 30.

Assuming that the signal is supplied by the switch 26 to the frequency multiplier 30, the signal's frequency is multiplied by a factor of two in the circuit 30 and is then supplied to a shaper circuit 32. After being reshaped to correct for distortions in the frequency multiplication process, the signal is again multiplied by a factor of two in a second frequency multiplier circuit 34 and is again reshaped in a shaper circuit 36, after which it is supplied through a single pole doublethrow switch 38 to one side of a balance potentiometer 40. The switch 38 allows one end of the rheostat 40 to be connected either to the output of the shaper 36 or to the output of the amplifier 28.

Similarly, the output of the bandpass filter 24 is coupled through a single pole doublethrow switch 42 to either the input of an amplifier 44 or through a series circuit of a frequency multiplier 46, a shaping circuit 48, a second frequency multiplier 50 and a shaper circuit 52 whose output is connected through a single pole doublethrow switch 54 to the other side of the balance potentiometer 40. The switch 54 allows the potentiometer to be selectively connected to the output of the shaper 52 or the output of the amplifier 44. The switches 42, 54, 26 and 38 are all ganged together so that the frequency multiplication in both the high and the low frequency channels can be selectively bypassed.

Each of the frequency multiplying circuits 30, 34, 46, and 50 multiplies the incoming frequency by a factor of two. Thus, over the lengths of the high and low frequency multiplication channels, the total multiplication factor is four.

There are various ways in which the frequency multiplication can be accomplished, including both digital and analog methods. Referring now more particularly to FIGS. 3 and 4, the details of one such frequency multiplication process will be described. Each frequency doubling circuit is essentially the same and thus only the frequency doubling circuit 30 will be described, it being understood that the other doubling circuits have similar configurations. The frequency doubling circuit 30 comprises a full-wave rectifier and accompanying bandpass filtering in the shaping circuit 32. Bandpass filtering is required to eliminate DC offset and to smooth waveform cusps produced by rectification of the signal. A gain stage is also included in the wave shaping circuit 32 to compensate for signal attenuation after rectification and filtering.

The full-wave rectifier, as shown in FIG. 3, is made up of two operational amplifiers 56 and 58. The amplifier 56 is connected to operate as a halfwave rectifier with the input signal being supplied to its inverting input through a resistance 64 having a value of R. The output of the amplifier 56 is connected to the cathode of a diode 60 whose anode is connected through a resistance 66, having a value R, to the inverting input of the amplifier 56. The output of the amplifier 56 is also connected to the anode of a diode 62 whose cathode is connected directly to the inverting input of the amplifier 56.

The anode of the diode 60 is connected through a resistance 68, having a value of one half R, to the inverting input at the amplifier 58. The non-inverting input of the amplifier 58 is connected through a resistance 72, having a value of one quarter R, to the circuit ground. The inverting input of the amplifier 58 is also connected through a resistance 70, having a value R, to the signal input to the circuit. The inverting input of the amplifier 58 is also connected through a resistance 74, having a value R, to the output of the amplifier 58.

The second amplifier 58 is connected to operate as an inverting, summing amplifier. The input signal is added to the half wave rectified signal to obtain a fully rectified signal, assuming the proper choice of resistances 68, 70, 72, and 74 on the inputs of the summing amplifier 58. Referring now more particularly to FIG. 4, it can be seen that, if the waveform 76 of the input signal to circuit 30 is basically sinusoidal, the output from the full-wave rectification will be a waveform 78 in which the negative going half cycle has been inverted to be positive going. After filtering in the shaping circuit 32, the cusp between the two halves will be eliminated and a waveform 80 having double the frequency of the waveform 76 will be produced, which is approximately sinusoidal.

Referring again to FIG. 2, the output from the contact arm of the potentiometer 40 is supplied to the input of a summing amplifier 82 whose output is connected to the pole of a single pole doublethrow switch 84. At one setting of the switch 84, the output from the amplifier 82 is supplied as the monophonic input to an amplifier 86 which drives a set of earphones 88. At the other setting of the switch 84, the signal output from the amplifier 82 is supplied as the input to left and right lateral modulation circuits 90 and 92, respectively, whose gains are responsive to left and right modulation control signals 94 and 96, respectively. It will be appreciated that the circuits 90 and 92 could comprise off the shelf transistor amplifier circuits whose gains are eletronically controllable, however in the disclosed embodiment, they are comprised of commercially available multiplier circuits.

As will now be described in greater detail with reference to FIGS. 2 and 5, the control signals 94 and 96 vary inversely with respect to each other and are essentially ramp waveforms to cause the output of for example, the left modulation circuit 90, to steadily increase over the heart beat and the output of the right modulation circuit 92 to simultaneously, steadily decrease. This will have the effect of making the heart beat sound appear to the listener as travelling from right to left. Of course, in other embodiments, the slopes of the right and left output control signals could be reversed so that the heart beat sounds would seem to the listener as coming from left to right. The primary advantage in having the sounds appear to travel from left to right is their physical correspondence to a phonocardiogram in which the beginning sounds of the heart cycle appear at the left end of the diagram, and the trailing ends of the heart cycle sounds appear at the right of the diagram.

The generation of the left and right control signals is accomplished by the following circuitry. A pair of standard electrocardiogram electrodes (not shown) detect heart beat signals 98 (see FIG. 5) in the standard fashion. Alternatively, finger electrodes or even electrodes on the chest piece could be used. These heart beat signals are supplied through an isolator circuit 100 to a bandpass filter 102. The output of the bandpass filter is amplified in an amplifier 104 and is differentiated by a differentiation circuit 106 to derive a spike representative of the QRS spike shown in waveform 98 of FIG. 5. A threshold detector circuit 108 is supplied with the differentiated output from the circuit 106. The threshold detector 108 can be any of a number of standard circuits, such as a Schmitt trigger. The output of the threshold detector is a pulse which passes through a blanking circuit 110. The purpose of the blanking circuit is to prevent any further pulses from being passed through for approximately 300 milliseconds. Thus, the circuit 110 is essentially a gate delay. The pulse passing through the circuit 110 is supplied to a trigger generator 112 which supplies the control pulse to the reciprocal wave generator 114. Trigger generator circuit 112 provides a pulse having a specified height and width and can be, for example, a monostable multivibrator. The reciprocal wave generator can be, for example, a differential amplifier connected to be in the integrating mode. Thus, the incoming square wave pulse from the trigger generator 112 will be integrated to produce the ramp waveform 94 shown in FIG. 5. By means of an inverter, this same integrated waveform will produce the oppositely directed ramp waveform 96 shown in FIG. 5.

The output of the trigger generator 112 is also supplied to a heart rate calculator 116 and to an LED driver 118 which energizes a light emitting diode 120 with each QRS pulse. The indicator 120 could be mounted any place within convenient view of the physician, but is preferably mounted on the transducer 16. The heart rate calculator can be, for example, a frequency-to-voltage converter which adjusts the slope of the ramp waveforms 94 and 96 to ensure a full spacial separation, independent of heart beat cycle length. The frequency multiplied, stereophonic output can be recorded on a standard stereo cassette tape recorder for archival and review purposes. Such recorders have not proven satisfactory in the past for recording heart sounds because they have a limited low frequency response. The frequency multiplication feature of the present invention overcomes this problem.

While, in the forgoing description, the features of frequency multiplication, lateral modulation, and visual indication of the heart rate are all shown as combined in a single device, it will be appreciated that each of these features has independent value.

Referring now more particularly to FIGS. 7, 8, 9, and 10, an embodiment of the electronic stethoscope is illustrated in detailed form. In some respects, the schematic diagram of FIGS. 7-10, inclusive, differs from the embodiment shown in FIG. 2 in that it omits certain functions shown in block form and incorporates other functions shown in block form and, also, incorporates in a single circuit, functions shown in separate blocks of FIG. 2, as will be explained in greater detail hereinafter.

Referring more particularly to FIG. 7, as explained in reference to the block diagram of FIG. 2, the microphone 16 detects sound waves and converts them into electrical signals which are supplied to the inputs of a pair of amplifiers 122 which are connected to have a high gain and high input impedance. The outputs of the amplifiers 122 are supplied to the inverting and non-inverting inputs of a differential amplifier 124 whose output is supplied to an RC circuit constituting the low pass portion of the filter 18 shown in FIG. 2. The output of the filter 18 is supplied to the non-inverting input of the operational amplifier 20. The characteristics of the amplifiers 124 and 120 constitute the high pass portion of the bandpass filter 18. The output of the amplifier 20 is supplied to the high pass filter 24 and the low pass filter 22.

The construction of the high pass and low pass channels shown in FIGS. 8 and 9 are substantially similar and thus only the circuitry of the high pass channel will be described, it being understood that the low pass channel operates in fundamentally the same manner. Bandpass filter 24 which has a bandpass of 120 to 240 Hz is made up of a pair of amplifiers connected in series to form a low pass filter 126 which passes all frequencies below 240 Hz and substantially attenuates all frequencies above 240 Hz. The filter 126 is followed by a second pair of amplifiers connected in series to form a high pass filter 128 which substantially attenuates all frequencies below 120 Hz and passes everthing above that frequency. The net result of the filters 126 and 128 is the bandpass filter 24 having a range of 120 to 240 Hz.

The output of the bandpass filter 24, unlike the diagram shown in FIG. 2 is fed directly to the input of a first frequency doubling circuit 46. It will be noted that the frequency doubling circuit 46 is somewhat different from the circuit 30 shown in FIG. 3. The operation, however, is substantially the same. A first amplifier is connected to operate as a half wave rectifier which amplifies the half wave rectified pulses by a factor of two. The next amplifier subtracts the original input signal from this double output to produce the waveform 78 shown in FIG. 4. The output from the first doubling circuit 46 is then supplied to the first half of the wave shaping circuit 48 which constitutes a pair of amplifiers connected to form a low pass filter 130 which not only smooths the cusps in FIG. 4 but also attentuates somewhat signals having frequencies above 480 Hz according to the slope of the filter.

The second half of the wave shaping circuit 48 is a pair of amplifiers connected in series to form a high pass filter 132 which somewhat attenuates all frequencies below 240 Hz. As explained in the text above, the purpose of the wave shaping circuit 48 is to correct for distortions in the frequency multiplication process. It should be kept in mind that the filters 126, 128, 130, and 132 do not completely attenuate frequencies outside of their bandpass frequencies and thus some of the upper and lower frequency sounds will be passed through.

The output of the high pass filter 132 is supplied to a second frequency doubling circuit 50 and finally is fed to a second wave shaping circuit 52 to construct it substantially in the same form as the wave shaping circuit 48, namely a 960 Hz low pass filter followed by a 480 Hz high pass filter.

Referring now more particularly to FIG. 10, the outputs of the high pass and low pass channels, as described above, are fed to opposite sides of a potentiometer. The contact arm of the potentiometer 40 supplies the signal, as selected by the position of the contact arm, to the input of an amplifier 82 whose output is connected to the inputs of the left and right modulation circuits 90 and 92, respectively. These modulation circuits are constituted by a multiplier circuit, such as Motorola Model MC1595, for example. The property of such a circuit is to multiply two inputs to produce a single output, i.e. one input is modulated by the other.

The output of the amplifier 82 is also supplied to the inputs of separate amplifiers 86 connected through switches 84'. It will be noted that, in one position of the switches 84', the modulators 90 and 92 are completely bypassed whereas in the other position of the switches 84', the modulation circuits 90 and 92 are placed in series with the amplifiers 86 so that the modulation circuits 90 and 92 are in effect. The outputs of the amplifiers 86 are supplied to the head sets 88 shown in FIG. 2.

The ECG signal, after passing through the isolator 100 and a bandpass filter 102 (not shown in FIG. 10) is applied to the inputs of a pair of differential amplifiers 138 connected in a high gain, high input impedance configuration. The outputs of these amplifiers are fed to the inputs of the differential amplifier 104 whose output is connected through an RC differentiation circuit 106 to the input of an amplifier 140. The output of the amplifier 140 is fed to the minus input of a first comparator 144 and to the plus input of a second comparator 146. A reference voltage VREF is supplied to the positive input of the comparator 144 and, through an inverter 142, to the negative input of the comparator 146. The outputs of the comparators 144 and 146 are connected together at a common point 148.

In operation, the comparators 144 or 146 compare the pulse output from the amlifier 140 with VREF and output a pulse at 148 if the output of the amplifier 140 exceeds the VREF. The purpose of having two comparators 144 and 146 is that it sometimes happens that the connections to the ECG electrodes on the patent's body are reversed so that the pulse output from the amplifier 144 may be either negative going or positive going. The comparators 144 and 146 are designed to give an absolute value output signal at the point 148 regardless of the polarity of the output of the amplifier 140.

An LED 120 is connected between the point 148 and the circuit ground and therefore will be energized with each pulse at the point 148. It will be noted that the blanking circuit 110, the trigger generator 112, and the LED driver 118 are omitted in the embodiment depicted in FIG. 10.

The trigger output signal from point 148 is also supplied to the input of a frequency to voltage converter 116 and the inverting input of a comparator 149. The output of the comparator 148 controls an FET switch 150 connected in parallel as an integrating capacitor 152 in the feed back loop of an amplifier 160. In operation, the frequency to voltage converter 116 converts each QRS pulse output at the point 148 into a corresponding voltage level. The converter 116 can be a standard integrated circuit such as National Semiconductor part No. LM2907 or LM2917.

The output of the frequency to voltage converter 116 is supplied to the input of the integrating circuit comprised of the amplifier 160 and the capacitor 152 so that a ramp waveform output results from the amplifier 160. Upon the receipt of each new QRS pulse, the comparator 149 and the FET switch 150 reset the integrated circuit. Thus, both the slope and the frequency of the ramp waveform are adjusted for the heartbeat rate.

It will be noted that the input to the amplifier 160 is applied to the inverting terminal and therefore the output is actually a negative ramp waveform 96 which is supplied as one input to the multiplier 92. After passing through an inverter 162, the output of the integrator 160 is also supplied as a positive going waveform 94 to one input of the multiplier 90. As described above, the outputs of the amplifiers 86' connected to the mutipliers 90 and 92 will be the heat sounds which seem to the hearer to sweep from the right to the left side.

While in the above-described embodiment, only two channels of frequency multiplication have been described, in other embodiments, more or fewer channels could be utilized. Also, the frequency could be multiplied by a factor other than two to place thr original sounds in the frequency range of 100 Hz to 4000 Hz. Further, the stethoscope of the invention can be advantageously used in any stethoscope application and not just for listening to heart sounds.

The terms and expressions which have been employed here are used as terms of description and not of limitations, and there is not intention, in the use of such terms and expressions, of excluding equivalents of the features shown and described, or portions thereof, it being recognized that various modifications are possible within the scope of the invention claimed.

I claim:

1. An electronic stethoscope comprising
   a phonocardio transducer for converting physical vibrations into corresponding alternating current electrical signals,
   frequency multiplier means for multiplying the frequency of said signals by a predetermined number and,
   reproducer means supplied with said frequency multiplied signals for audibly reproducing said frequency multiplied signals.

2. An electronic stethoscope as recited in claim 1 wherein the frequency multiplier means multiplies the frequency of the phonocardio transducer signals by a predetermined integer.

3. An electronic stethoscope as recited in claim 2 wherein the integer is four.

4. An electronic stethoscope as recited in claim 1 wherein the reproducer means includes separate, left and right sound reproducers, further comprising
   electrocardio detection means for detecting and amplifying electrical signals generated within a patient by the patient's heart motion,
   detection circuitry supplied with said detected and amplified heart electrical signals for detecting the QRS wave thereof and for producing a trigger control pulse in response thereto,
   stereophonic amplification circuitry, supplied with the frequency multiplied, phonocardio signals, for driving the left and right sound reproducers, the stereophonic amplification circuitry having left and right amplification channels whose gains are independently modulated by left and right control signals, respectively, and
   a reciprocal wave generator supplied with the trigger control pulse for generating, in response thereto, left and right control signals, whose waveforms are inverted with respect to each other, for the stereophonic amplification means whereby the amplified, frequency multiplied phonocardio signals, when audibly reproduced, are perceived as shifting from one of the sound reproducers to the other over the period of each heart beat.

5. An electronic stethoscope as recited in claim 4 further including a heart rate calculator supplied with the trigger control pulse for determining the heart rate and for adjusting the rate of change with respect to time of the left and right control signals as a predetermined function of the detected heart rate.

6. An electronic stethoscope as recited in claims 4 or 5 wherein the reciprocal wave generator generates left and right control signals having ramp waveforms which have oppositely directed slopes.

7. An electronic stethoscope as recited in claim 1 wherein the frequency multiplier means comprises a plurality of bandpass filters for dividing the phonocardio transducer signals into a plurality of component frequency ranges and separately frequency multiplies the component frequency ranges.

8. An electronic stethoscope as recited in claim 7 further comprising potentiometer means supplied with the frequency multiplied component frequency ranges for providing a balance control selection of the portion of each range to be audibly reproduced.

9. An electronic stethoscope as recited in claim 1 wherein the frequency multiplier means comprises
   a full wave rectifier circuit,
   a band pass filter, and
   a wave shaping circuit connected in series through the bandpass filter to the fullwave rectifier circuit, whereby the bandpass filter and wave shaping circuit eliminate DC offset and smooth waveform cusps produced by rectification of the phonocardio transducer signal.

10. An electronic stethoscope as recited in claim 9 wherein the frequency multiplier means comprises a pair of such series connected circuits.

11. An electronic stethoscope comprising
   a phonocardio transducer for converting physical vibrations into corresponding alternating current electrical signals,
   electrocardio detection means for detecting and amplifying electrical signals generated within a patient by the patient's heart,
   detection circuitry supplied with said detected and amplified heart electrical signals for detecting the QRS wave thereof and for producing a trigger control pulse in response thereto,
   stereophonic reproduction means supplied with the signals detected by the phonocardio transducer, for stereophonically, audibly reproducing such signals, the stereophonic reproduction means having left and right amplification channels whose outputs are independently modulated in response to left and right control signals, respectively, and
   a reciprocal wave generator supplied with the trigger control pulse for generating, in response thereto, left and right control signals, whose waveforms are inverted with respect to each other, for the stereophonic reproduction means whereby the amplified phonocardio signals shift from one reproduction channel to the other over the period of each heart beat.

12. An electronic stethoscope as recited in claims 4 or 11 further comprising a signal lamp connected to be energized by the trigger control pulse, the signal lamp being mounted on the phonocardio transducer.

13. An electronic stethoscope as recited in claim 11 further including a heart rate calculator supplied with the trigger control pulse for determining the heart rate and for adjusting the rate of change with respect to time of the left and right control signals as a predetermined function of the detected heart rate.

14. An electronic stethoscope as recited in claim 11 wherein the reciprocal wave generator generates left and right control signals having ramp waveforms which have oppositely directed slopes.

15. A method of electronically processing subaudile sound signals comprising the steps of
    converting the sound signals to corresponding alternating current electrical signals,
    multiplying the frequency of such signals by an integer sufficient to place such signals in the frequency range of 100 Hz to 4000 Hz,
    amplifying the frequency multiplied signals, and
    audibly reproducing the frequency multiplied signals.

16. A method of electronically processing subaudible sound signals as recited in claim 15 wherein the converting step includes converting the heart sounds of a patient into alternating current electrical signals, and further comprising the steps of detecting electrocardio signals from the patient, detecting the QRS pulse thereof, producing an electrical pulse in response thereto, integrating said electrical pulse with respect to time to produce a signal having a ramp shaped waveform, modulating the frequency multiplied signals with the ramp waveform signal and audibly reproducing the result at a first location, and modulating the frequency multiplied signals with the inverse of the ramp waveform signal and audibly reproducing the result at a second location which is physically spaced apart from the first location to give a stereo movement effect.

* * * * *